(12) United States Patent
Corma Canós et al.

(10) Patent No.: US 6,916,459 B2
(45) Date of Patent: Jul. 12, 2005

(54) ZEOLITE ITQ-16

(75) Inventors: Avelino Corma Canós, Valencia (ES); Maria Teresa Navarro Villalba, Valencia (ES); Fernando Rey García, Valencia (ES); Susana Valencia Valencia, Valencia (ES)

(73) Assignees: Consejo Superior De Investigaciones Cientificas, Madrid (ES); Universidad Politecnica De Valencia, Valencia (ES)

( * ) Notice: Subject to any disclaimer, the term of this patent is extended or adjusted under 35 U.S.C. 154(b) by 0 days.

(21) Appl. No.: 10/412,624

(22) Filed: Apr. 11, 2003

(65) Prior Publication Data

US 2004/0042958 A1 Mar. 4, 2004

Related U.S. Application Data

(63) Continuation of application No. PCT/ES01/00387, filed on Oct. 11, 2001.

(30) Foreign Application Priority Data

Oct. 11, 2000 (ES) .......................................... 200002537

(51) Int. Cl.$^{7}$ ............................................. C01B 39/48
(52) U.S. Cl. ...................... 423/718; 423/705; 423/706; 423/708; 208/111.01; 208/120.01; 208/135; 585/467; 585/722; 585/732; 568/300; 549/529; 549/531
(58) Field of Search ................................ 423/718, 713, 423/706, 708, 705

(56) References Cited

U.S. PATENT DOCUMENTS

| | | | |
|---|---|---|---|
| RE28,341 E | | 2/1975 | Wadlinger et al. |
| 4,826,667 A | * | 5/1989 | Zones et al. ................. 423/706 |
| 6,409,986 B1 | * | 6/2002 | Camblor Fernandez et al. ........................... 423/705 |
| 6,733,742 B1 | * | 5/2004 | Elomari ....................... 423/706 |

OTHER PUBLICATIONS

Beta family, polymorph A (*BEA)—polymorph B; Zeolites 16:323–802; 1996, p. 641.

Perez–Pariente et al; Crystallization Mechanism of Zeolite Beta From (TEA)$_2$O, Na$_2$O and K$_2$O Containing Aluminosilicate Gels; Applied Catalysis, 31 (1987) pp. 35–64.

Newsam et al; Structural Characterization of Zeolite Beta; Proc. R. Soc. Lond. (1988) pp. 375–405.

Corma et al., ITQ–16, a new zeolote family of the beta group with differnet proporitions of polymorphs A,B and C, Chem. Comm., 2001, ISSN 1359, 1720–1721.

* cited by examiner

*Primary Examiner*—David Sample
(74) *Attorney, Agent, or Firm*—Klauber & Jackson

(57) ABSTRACT

This invention refers to a new zeolitic material included under the ITQ-16 denomination, to the method for obtaining them and their use as catalysts.

This material, ITQ-16 zeolite, is characterized by having different ratios of the different polymorphs A, B and C described as possible intergrowths in Beta zeolite and which, therefore, show different X-ray diffraction patterns to that described for Beta zeolite, showing the X-ray diffraction pattern for ITQ-16, as it is synthesised, diffraction peaks at 2θ angles of 6.9°, 7.4°, and 9.6°, simultaneously.

ITQ-16 zeolite in its calcinated form has the following empiric formula:

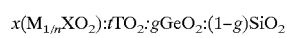

$$x(M_{1/n}XO_2):tTO_2:gGeO_2:(1-g)SiO_2$$

where T is one or various elements with +4 oxidation status, different of Ge and Si; X is one or various elements with +3 oxidation status and M can be H$^+$ or one or various inorganic cations with charge +n, t is comprised between 0 and 0.1, g is comprised between 0.001 and 0.33 and x is comprised between 0 and 0.2.

26 Claims, 11 Drawing Sheets

DABCO-benzyl

Q-benzyl

TEA

ZEOLITE ITQ-16

This is a continuation of PCT/ES01/00387, filed Oct. 11, 2001.

TECHNICAL FIELD

BACKGROUND

Beta zeolite is a microporous material with channels formed by rings with 12 members, presenting a characteristic diffraction pattern that is shown in FIG. 1 (Pérez-Pariente, J., Martens, J. A., Jacobs, P. A., Applied Catalysis, 31 (1987) 35).

Zeolite is formed by an intergrowth of different polymorphs interrelated with each other, as has been described in the literature (J. M. Newsam, M. M. J. Treacy, W. T. Koetsier, C. B. de Gruyter, Proc. R. Soc. London A, 420 (1998) 375). From all the polymorphs described, it seems that polymorphs A and B are the ones that basically make up the intergrowth denominated Beta zeolite (Zeolites, 5/6, (1996), 641) while polymorph C (whose diffractogram, calculated from the structure proposed in J. M. Newsam, M. M. J. Treacy, W. T. Koetsier, C. B de Gruyter, Proc. R. Soc. London A, 420 (1998), 375 is shown in FIG. 2) shows a lower proportion of this intergrowth.

Therefore, it should be possible to synthesize new materials with different ratios of the different polymorphs A, B and C that would lead to structures with an X-ray diffractogram different from that of Beta zeolite as defined according to its X-ray diffractogram, and different from that of the pure C polymorph.

In this invention, a material that is included under the denomination of ITQ zeolite, which is characterized by its X-ray diffractogram and which seems to indicate that the materials of this group have different ratios of the different polymorphs A, B, and C described as possible intergrowths in the Beta zeolite, therefore, show different X-ray diffraction patterns to that described for Beta zeolite.

DESCRIPTION OF THE INVENTION

The present invention refers to a new zeolitic material that are included within the ITQ-16 denomination, to the method for obtaining it, and to its catalytic applications.

ITQ-16 zeolite is related to Beta zeolite but presents a different X-ray diffractogram, shown in FIG. 3, that can be due to the presence of a different ratio of the various polymorphs, to that found in Beta zeolite, which diffractogram is shown in FIG. 1. In this way, ITQ-16 zeolite could be made up, apart from polymorphs A and B characteristic of Beta zeolite, of another polymorph that could correspond to the C polymorph proposed by Newsam (J. M. Newsam, M. M. J. Treacy, W. T. Koetsier, C. B. de Gruyter, Proc. R. Soc. London A, 420 (1998) 375). Therefore, the presence of this other polymorph confers an X-ray diffraction pattern on the ITQ-16 material that is different from that of Beta zeolite.

The X-ray diffraction pattern for ITQ-16 zeolite, as synthesized, shows the following angle 2θ and relative intensity, I/Io, values:

| 2θ (degrees) | Intensity |
|---|---|
| 6.93 | w-vs |
| 7.44 | w-vs |
| 9.58 | w-vs |
| 19.32 | w |
| 21.12 | m |
| 21.93 | s |
| 22.19 | vs |
| 25.12 | w |
| 27.15 | w |
| 27.94 | w |
| 28.43 | w |
| 29.46 | w |
| 29.99 | w |
| 32.98 | w |
| 33.11 | w |
| 34.68 | w |
| 35.76 | w |
| 37.12 | w | where w means an intensity between 0.001 and 20%; m means medium intensity, between 20 and 40%; s means strong intensity, between 40 and 60%, and vs means very strong intensity, between 60 and 100% and w-vs indicates that the relative intensity of these peaks can vary depending on the proportion of polymorphs. The relative positions, widths and intensities of the diffraction peaks can be modified according to the chemical composition of the material (type of structure directing agent, Si/Ge ratio, presence of other trivalent and/or tetravalent hetero-atoms (one or various) in the network, apart from silicon and germanium, as for example: aluminium, boron, titanium, vanadium, etc.), together with the degree of hydration and the size of the crystal.

The X-ray diffraction pattern of the ITQ-16 material, as synthesised, has been obtained in a Philips PW 1830 diffractometer with a PW 1710 controller and Cu Kα radiation. The diffractogram obtained—for a specific sample of ITQ-16 exclusively made up of Si and Ge oxide with Si/Ge ratio=50 m—by means of the powder method and using a fixed divergence slit, is characterized by the following values shown in Table 1, by the angle 2θ (degrees) and relative intensities (I/Io), with $I_o$ being the intensity of the most intense peak, which is assigned a value of 100. The relative intensities have been expressed in the following terms: w=weak intensity (between 0.001 and 20%); m=medium intensity (between 20 and 40%); s=strong intensity (between 40 and 60%) and vs=very strong intensity (between 60 and 100%).

TABLE I

| 2θ (degrees) | Intensity |
|---|---|
| 6.93 | s |
| 7.44 | m |
| 9.58 | w |
| 19.32 | w |
| 21.12 | m |
| 21.93 | s |
| 22.19 | vs |
| 25.12 | w |
| 27.15 | w |
| 27.94 | w |
| 28.43 | w |
| 29.46 | w |
| 29.99 | w |
| 32.98 | w |
| 33.11 | w |

TABLE I-continued

| 2θ (degrees) | Intensity |
|---|---|
| 34.68 | w |
| 35.76 | w |
| 37.12 | w |

In particular, the pattern shown in table I above and in FIG. 3 refers to materials whose network is exclusively made up of silica and germanium oxide, with Si/Ge ratio=50 and synthesised using the DABCO-benzyl cation, whose structure is shown in FIG. 4, as the structure directing agent.

Table II shows the values of angle 2θ and relative intensities ($I/I_o$) of the powder reflections on the X-ray diffractogram for the previous sample after having been calcinated at 580° C. to eliminate organic compounds occluded inside the zeolite, where w, m, s and vs have the same meanings as in table I.

TABLE II

| 2θ (degrees) | Intensity |
|---|---|
| 7.01 | vs |
| 7.52 | vs |
| 9.61 | m |
| 11.63 | w |
| 13.41 | w |
| 14.37 | w |
| 15.49 | w |
| 19.33 | w |
| 21.31 | w |
| 22.35 | vs |
| 25.23 | w |
| 25.87 | w |
| 27.06 | w |
| 28.26 | w |
| 28.54 | w |
| 29.50 | w |
| 30.31 | w |
| 33.27 | w |
| 34.67 | w |
| 36.04 | w |
| 37.18 | w |

The X-ray diffraction pattern of the ITQ-16 zeolite is mainly differentiated from that of Beta zeolite in that, at low angles, it shows, apart from a wide peak around a value of 2θ of 7.4°, two peaks at angle 2θ of 6.9°, and 9.6, that, in general, show a smaller width at medium height than the peak at 7.4°. The three mentioned peaks are individual peaks that can be identified in the X-ray diffraction diagram as can be seen in FIG. 3. The relative intensity of the peaks at 6.9° and 9.6° with regard to the peak at 7.4° complies with the $I_{9.6°}/I_{7.4°}$ ratio and the $I_{6.9}/I_{7.4}$ ratio being greater than zero and less than ∞.

The relative intensity of these peaks varies as the ratio of polymorphs A, B and C varies in the structure of the ITQ-16 zeolite. With the limits being those of pure polymorph C, proposed by Newsam (FIG. 2), and Beta zeolite (FIG. 1) (Pérez-Pariente, J., Martens, J. A., Jacobs, P. A., Applied Catalysis, 31 (1987) 35) (U.S. Pat. No. Re28,341).

Therefore, this invention refers to a material that has the Beta zeolite and another polymorph that could be polymorph C as its extreme limits. In Beta zeolite and the possible polymorph C, as opposed to that occurring with the ITQ-16 zeolite, the peaks at angles 6.9°, 7.4° and 9.6° are not simultaneously found.

The material in its calcinated form has the following empiric formula:

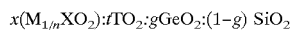

wherein T is one or various elements different from Ge and Si with oxidation status +4, such as Ti, V, Sn; X is one or various elements with oxidation status +3 such as Al, Ga, B, Cr, Fe; and M can be $H^+$ or one or various inorganic cations with charge +n as for example $Li^+$, $Na^+$, $K^+$, $Ca^{2+}$, $Mg^{2+}$, etc; and wherein "t" is comprised between 0 and 0.1, "g" is comprised between 0.001 and 0.33 and "x" is comprised between 0 and 0.2.

As the synthesis composition necessary for synthesising the ITQ-16 zeolite depends on the structure directing agent employed, below is described the chemical composition range of the material ITQ-16 for specific embodiments of the invention, according to the structure directing agent.

In the case of using the TEA cation as structure directing agent, g must be between 0.33 and 0.001, preferably between 0.33 and 0.01. In the case of being synthesised with trivalent cations, as for example Al, the ITQ-16 zeolite is achieved when the Si+Ge/Al ratio, equivalent to 1/x, is between 5 and ∞, preferably greater than 15. To obtain the ITQ-16 zeolite with other tetravalent cations other than silicon and germanium, such as Sn, V, Ti, the $SiO_2+GeO_2/TO_2$ ratio must have a value between 10 and ∞, preferably between 20 and 1000.

When the DABCO-benzyl cation is used as structure directing agent, to obtain the ITQ-16 the g value must be between 0.17 and 0.001, and preferably between 0.032 and 0.001, and more preferably between 0.032 and 0.01. In the case of being necessary to synthesise ITQ-16 zeolite with trivalent cations, as for example Al, the ratio Si+Ge/Al will be between 5 and ∞, preferably greater than 15 and more preferably greater than 20.

To obtain ITQ-16 zeolite with other tetravalent cations other than silicon and germanium, such as Sn, V, Ti, the $Si_2+GeO_2/Al$ ratio must have a value between 5 and ∞, and preferably between 20 and 1000.

When a Q-benzyl cation is used as structure directing agent to obtain ITQ-16, g must have a value between 0.2 and 0.001, preferably between 0.134 and 0.001 and more preferably between 0.134 and 0.01. In the case of being necessary to synthesise ITQ-16 zeolite with trivalent cations, as for example Al, the ratio Si+Ge/Al will be between 5 and ∞, preferably greater than 15 and more preferably greater than 20. To obtain the ITQ-16 zeolite with tetravalent cations other than silicon and germanium, such as Sn, V, Ti, the $SiO_2+GeO_2/TO_2$ ratio must have a value between 10 and ∞, preferably between 20 and 1000.

The present invention refers to the process for obtaining the material denominated ITQ-16, characterized by means of a synthesis medium with a pH between 5 and 8.5, and preferably between 6 and 8, and the use of fluoride anions as mineralising agent, and TEA, DABCO-benzyl and Q-benzyl cations as structure directing agents.

The preparation method is based on heating at temperatures between 110° C. and 200° C., and preferably between 130° C. and 175° C., of a reaction mixture containing a source of Si, amongst which amorphous silica, colloidal silica, silica gel, tetraalkylorthosilicate are preferred, and a source of germanium such as, for example, germanium oxide, halides or alcoxides. The synthesis mixture contains one or more of the following cations as structure directing agents: TEA, DABCO-benzyl, Q-benzyl and a source of $F^-$ ions.

Optionally, trivalent cations such as, for example, Al, B, Ga, Fe or Cr, and tetravalent cations such as Ti, V or Sn can be included in the synthesis gel.

The composition of the synthesis mixture is characterized by the following ranges of molar ratios when using the DABCO-benzyl cation as structure directing agent.
DABCO-benzyl/(SiO$_2$+GeO$_2$)=between 3 and 0.01, and preferably between 1 and 0.03.

H$_2$O/(SiO$_2$+GeO$_2$)=between 1000 and 0.5, and preferably between 100 and 2.
HF/(SiO$_2$+GeO$_2$)=between 3 and 0.01, and preferably between 1 and 0.03.
GeO$_2$/(SiO$_2$+GeO$_2$) defined as g=between 0.17 and 0.001, and preferably between 0.032 and 0.001, even more preferably between 0.032 and 0.01.
(Si+Ge)/X=between 5 and ∞, and preferably over 15, even more preferably over 20.
SiO$_2$+GeO$_2$/TO$_2$=between 10 and ∞, and preferably between 20 and 1000.
wherein X represents an element in its trivalent oxidation state, such as Al, B, Fe, Ga or Cr; and T represents an element in its tetravalent oxidation state, such as Ti, Sn or V.

When the TEA cation is used as structure directing agent, the composition of the synthesis mixture is characterized by the following molar ratios:

TEA/(SiO$_2$+GeO$_2$)=between 3 and 0.01, and preferably between 1 and 0.03.
H$_2$O/(SiO$_2$+GeO$_2$)=between 1000 and 0.5, and preferably between 100 and 2.
HF/(SiO$_2$+GeO$_2$)=between 3 and 0.01, and preferably between 1 and 0.03.
GeO$_2$/(SiO$_2$+GeO$_2$) defined as g=between 0.33 and 0.001, and preferably between 0.33 and 0.01.
(Si+Ge)/X=between 5 and ∞, and preferably over 15. SiO$_2$+GeO$_2$/TO$_2$=between 10 and ∞, and preferably between 20 and 1000.
where X represents an element in its trivalent oxidation state such as Al, B, Fe, Ga or Cr; and T is an element in its tetravalent oxidation state such as Ti, Sn or V.

When the Q-benzyl cation is used as structure directing agent, the composition of the synthesis mixture is characterized by the following molar ratios:

Q-benzyl/(SiO$_2$+GeO$_2$)=between 3 and 0.01, and preferably between 1 and 0.03.
H$_2$O/(SiO$_2$+GeO$_2$)=between 1000 and 0.5, and preferably between 100 and 2.
HF/(SiO$_2$+GeO$_2$)=between 3 and 0.01, and preferably between 1 and 0.03.
GeO$_2$/(SiO$_2$+GeO$_2$) defined as g=between 0.2 and 0.001, and preferably between 0.134 and 0.001, even more preferably between 0.134 and 0.01.
(Si+Ge)/X=between 5 and ∞, and preferably over 15, even more preferably over 20.
SiO$_2$+GeO$_2$/TO$_2$=between 10 and ∞, and preferably between 20 and 1000.
where X represents an element in its trivalent oxidation state such as Al, B, Fe, Ga or Cr; and T is an element in its tetravalent oxidation state such as Ti, Sn or V.

In the case of employing mixtures of benzyl-DABCO and Q-benzyl cations as structure directing agents, the composition of the synthesis mixture is characterized by the following ranges of molar ratios:

(DABCO-benzyl+Q-benzyl/(SiO$_2$+GeO$_2$)=between 3 and 0.01, and preferably between 1 and 0.03.

H$_2$O/(SiO$_2$+GeO$_2$)=between 1000 and 0.5, and preferably between 100 and 2.
HF/(SiO$_2$+GeO$_2$)=between 3 and 0.01, and preferably between 1 and 0.03.
GeO$_2$/(SiO$_2$+GeO$_2$) defined as g=between 0.2 and 0.001, and preferably between 0.134 and 0.001, even more preferably between 0.134 and 0.01.
(Si+Ge)/X=between 5 and ∞, and preferably over 15, even more preferably over 20.
SiO$_2$+GeO$_2$/TO$_2$=between 10 and ∞, and preferably between 20 and 1000.
DABCO-benzyl/(DABCO-benzyl+Q-benzyl)=between 0 and 1 both excluded.
where X represents an element in its trivalent oxidation state such as Al, B, Fe, Ga or Cr; and T is an element in its tetravalent oxidation state such as Ti, Sn or V.

Once the crystallisation is complete, the solids are separated from the mother liquor by filtering and/or centrifuging. As a result, a highly crystalline solid that contains occluded organic material is obtained.

The solid product obtained has a characteristic diffraction pattern (CuKα radiation) as shown in FIG. 3 and in table 1, which has a certain similarity to that of the Beta zeolite (U.S. Pat. No. Re28,341) at a high 2θ>20° angle, where θ is the Bragg angle, and little similitude at low angles.

The organic material and the occluded fluoride anions are eliminated by means of calcination in a vacuum, air, N$_2$ or another inert gas, at a temperature over 450° C., and preferably at a temperature over 500° C. and under 900° C. The X-ray diffraction pattern of the calcinated material is presented in FIG. 5 and in table 2.

In this way, the calcinated ITQ-16 zeolite shows a diffraction peak around 7.4°, characterized by a width at medium height of around 1° and characteristic of the Beta zeolite (Newsam et al., Proc. R. Soc. London A. 1988, 420, 375) with a determined intergrowth of A and B polymorphs, but also shows two peaks at 6.9° and 9.6° corresponding to the presence of another polymorph that could be polymorph C. Therefore, the ITQ-16 zeolite shows a different intergrowth to that of the Beta zeolite.

For the ITQ-16 zeolite synthesised in this report, the following uses are described:

As an additive of hydrocarbon catalytic cracking catalysts, and in general in organic compounds.

As a component of hydro-cracking and soft hydro-cracking catalysts.

As a component or additive of light paraffin isomerization catalysts.

As a component of de-paraffining and iso-paraffining catalysts.

As a catalyst for alkylation of isoparaffins with olefins and alkylation of aromatics and substituted aromatics with olefins and alcohols, and more specifically as a catalyst from the alkylation of benzene with propylene.

As catalyst in acylation reactions of aromatic compounds substituted using acids, acid chlorides or organic acid anhydrides as acylating agents.

As catalysts in Meerwein-Pondorf-Verley and Oppenauer reactions.

As a catalyst for the catalytic elimination of organic vapours (VOC).

In the case of the ITQ-16 containing Ti, its use is described as a catalyst for epoxidation of olefins, oxidation of alkanes, oxidation of alcohols and oxidation of thioethers to sulphoxides and sulphonates using organic or inorganic hydro-peroxides, as for example $H_2O_2$, tertbutylhydroperoxide, cumene hydroperoxide, as oxidating agents.

In the case of containing Sn its use is described as oxidating catalysts in Bayer-Villiger reactions using $H_2O_2$ as oxidating agent. Finally, its use is described in ammoximation of cyclohexanone to oxime with $NH_3$ and $H_2O_2$.

EXAMPLES

Example 1

This example shows the preparation of ITQ-16 containing Si and Ge, and using the DABCO-benzyl cation as the structure directing agent.

6.8 g of tetraethylorthosilicate (TEOS) are hydrolysed in 8.335 g of an aqueous solution of DABCO-benzyl ($2.10^{-3}$ mols of DABCO-benzyl(OH)/g) and 0.92 g of water. Then 0.0684 g of $GeO_2$ are added. The mixture is then left stirring and evaporating the ethanol formed in the hydrolysis of the TEOS. Finally, 1.334 g of HF (50% aq.) are added. The resulting mixture is heated at 150° C. in autoclaves lined internally with PTFE. After 13 h of heating, the mixture is filtered and 17 g of the ITQ-16 zeolite are obtained for each 100 g of synthesis gel.

Figure 1:
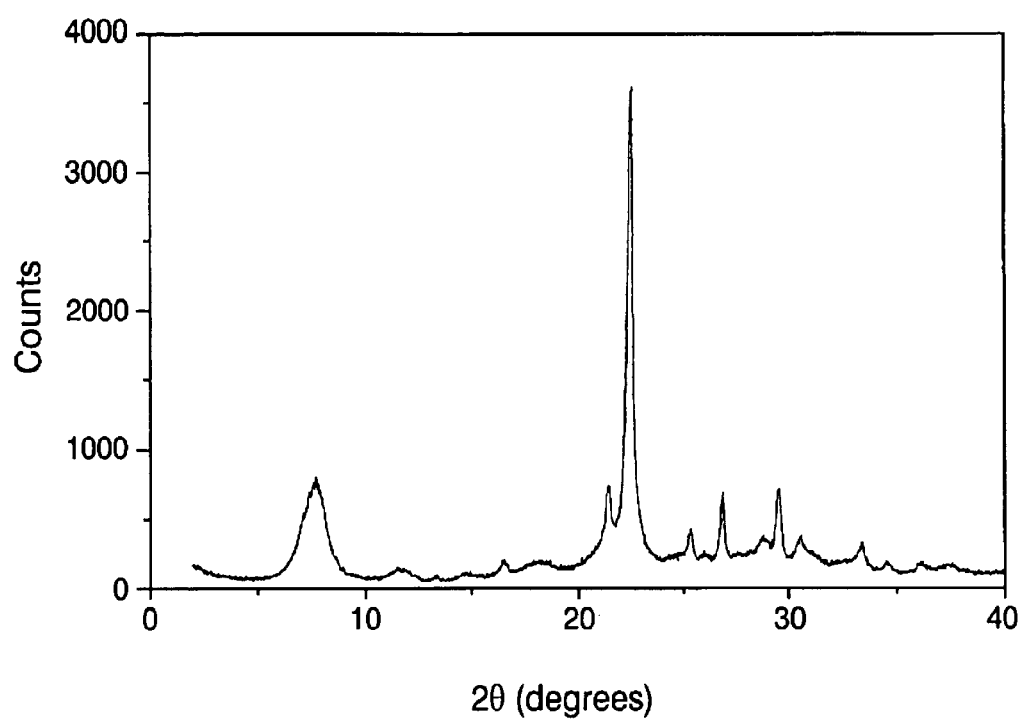
FIG. 1 represents a Beta zeolite X-ray diffractogram.
Figure 2:
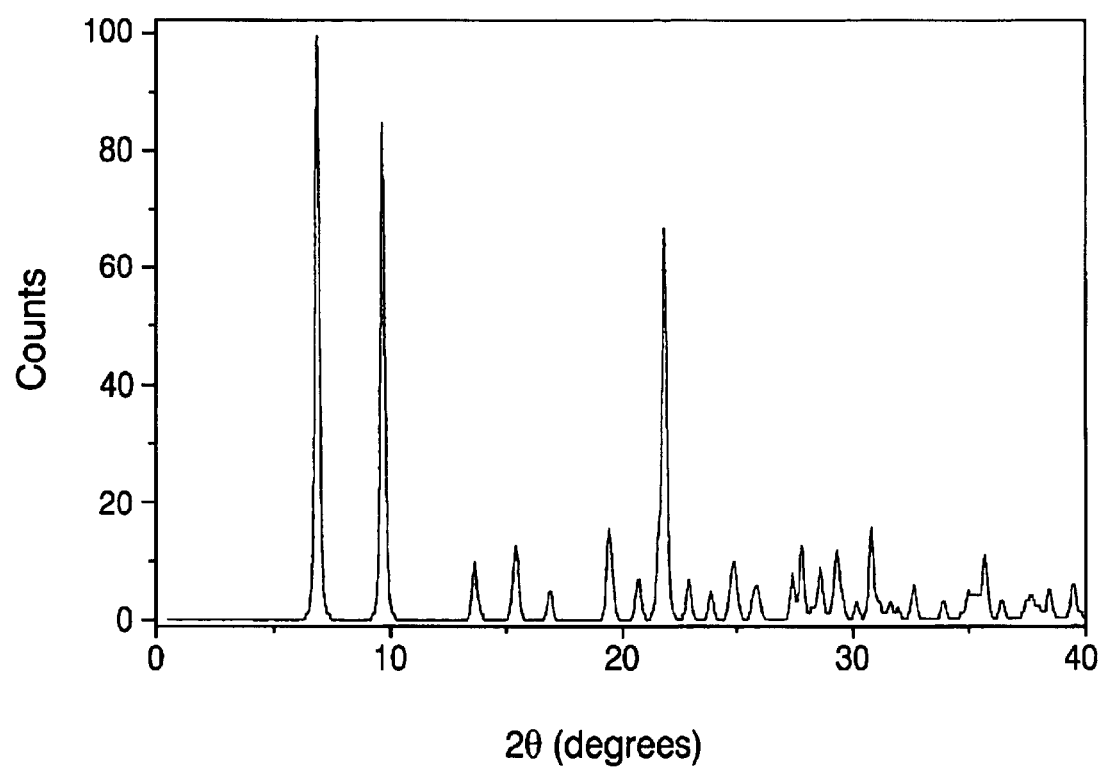
FIG. 2 represents the diffractogram calculated for polymorph C.
Figure 3:
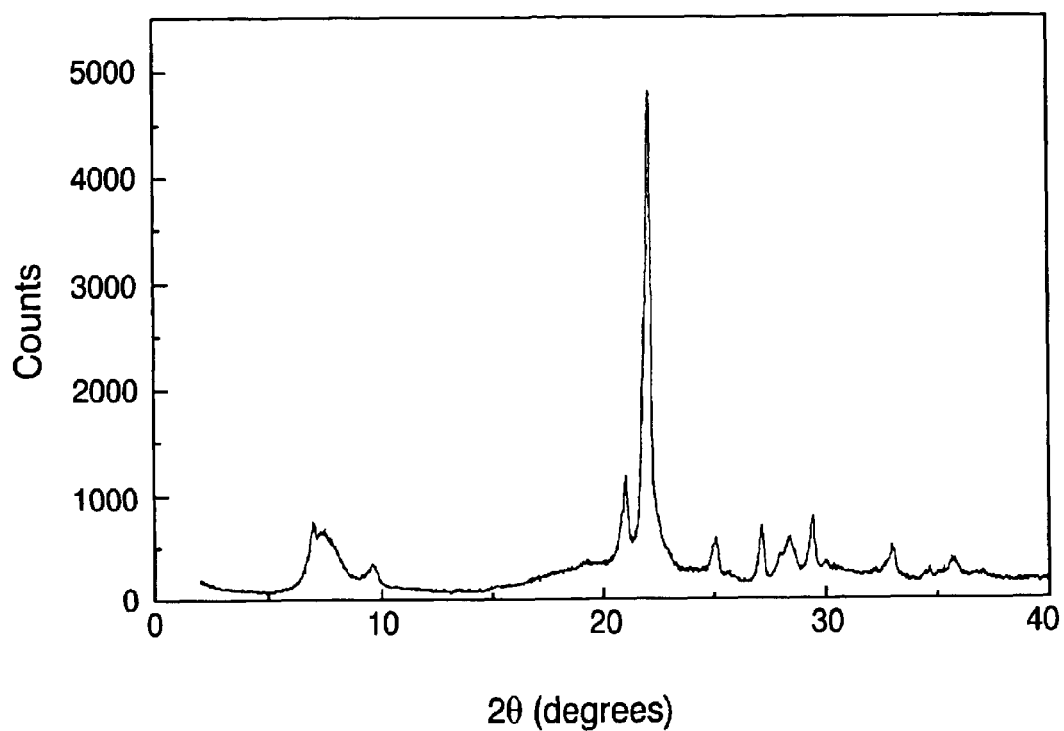
FIG. 3 shows a diffractogram of a material made up exclusively of silicon and germanium oxide, in a ratio of Si/Ge=50 and synthesised using the DABCO-benzyl cation.
Figure 4:
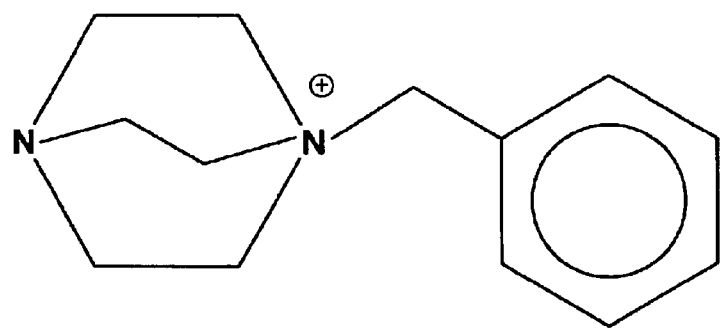
FIG. 4 shows the formulae for the cations used as structure directing agents.
Figure 4:
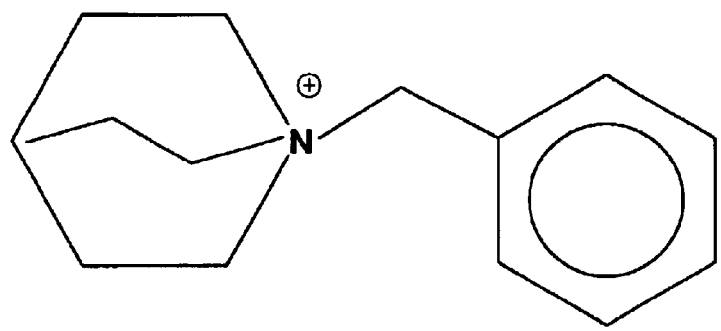
Figure 4:
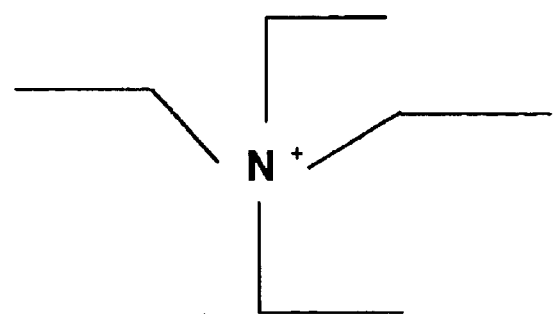
Figure 5:
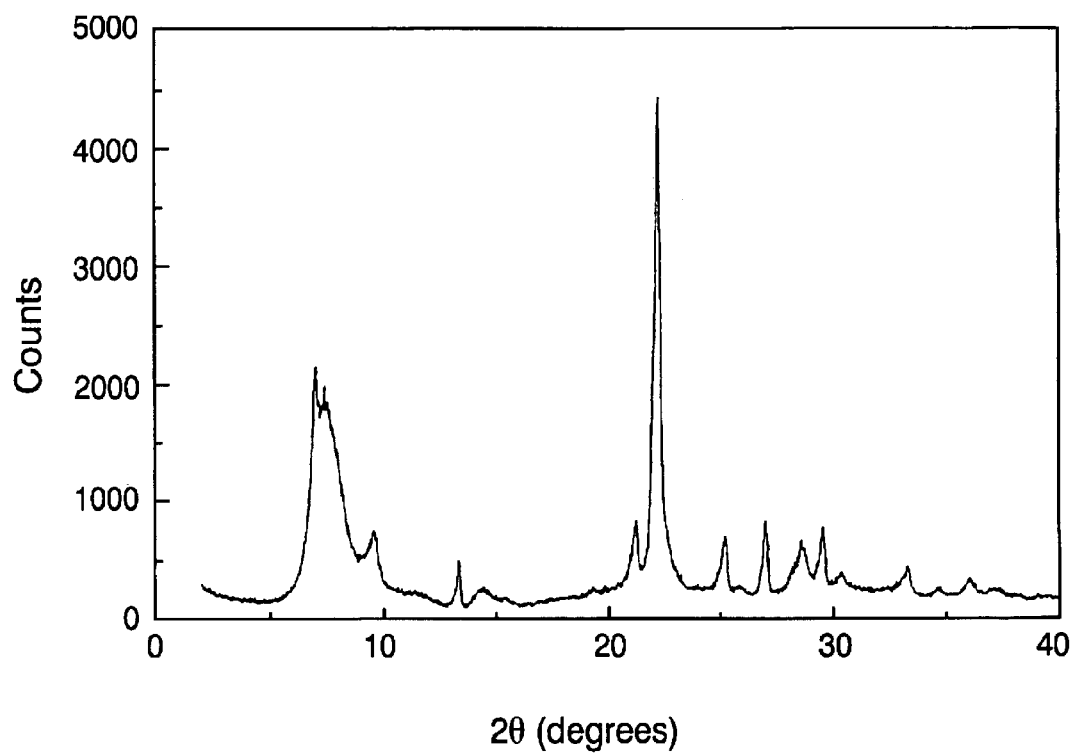
FIG. 5 shows the diffraction pattern of the calcinated ITQ-16 zeolite.

The X-ray diffraction pattern is shown in FIG. 3.

Example 2

This example shows the preparation of ITQ-16 containing Si, Ge and Al, and using the DABCO-benzyl cation as structure directing agent where (Si+Ge)/Al=50.

13.0 g of tetraethylorthosilicate (TEOS) are hydrolysed in 34.74 g of an aqueous solution of DABCO-benzyl ($9.98^{-4}$ mols of DABCO-benzyl(OH)/g). Then 0.436 g of $GeO_2$ and 0.272 g of aluminium isopropoxide are added. The mixture is then left stirring and evaporating the ethanol formed in the hydrolysis of the TEOS, and 15.25 g of water. Finally, 1.334 g of HF (50% aq.) are added. The resulting mixture is heated at 150° C. in autoclaves lined internally with PTFE. After 46 h of heating, the mixture is filtered and 20 g of the ITQ-16 zeolite are obtained for each 100 g of synthesis gel.

Figure 6:
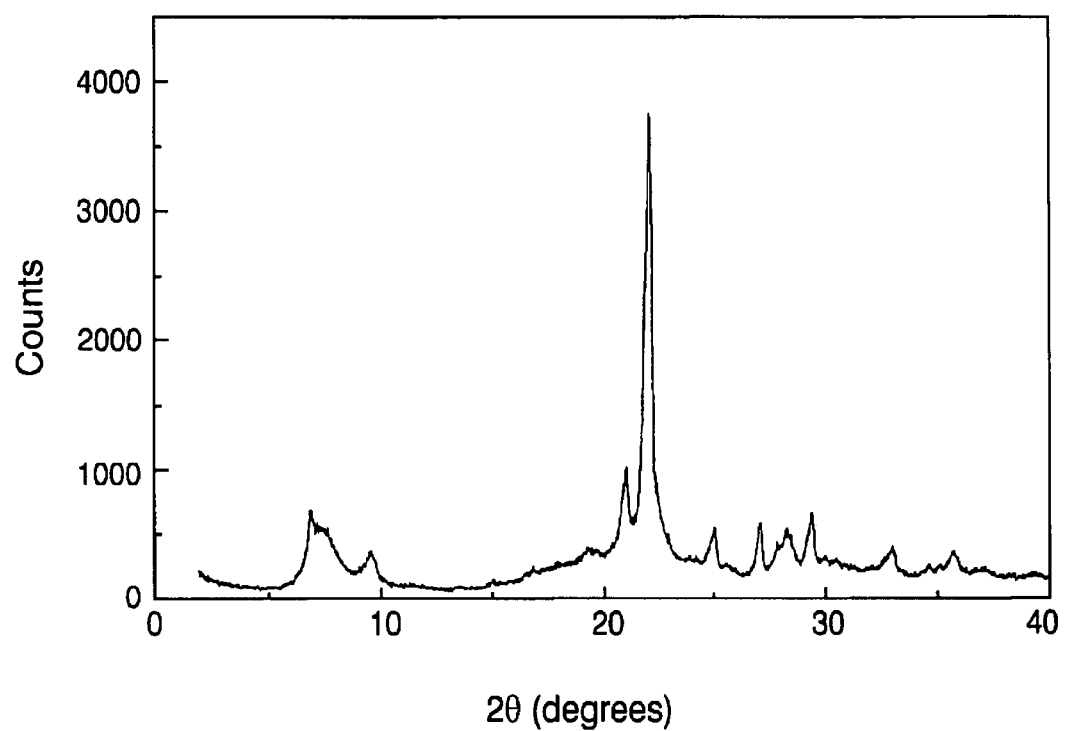
FIG. 6 shows the diffraction pattern of ITQ-16 prepared according to example 2, with (Si+Ge)/Al=50 and using the DABCO-benzyl cation as structure directing agent.

The X-ray diffraction pattern is shown in FIG. 6.

Example 3

This example shows the preparation of ITQ-16 containing Si and Ge, and using the Q-benzyl cation as structure directing agent.

6.511 g of tetraethylorthosilicate (TEOS) are hydrolysed in 8.29 g of an aqueous solution of Q-benzyl ($2.0.10^{-3}$ mols of Q-benzyl(OH)/g). Then 0.218 g of $GeO_2$ and 0.7 g of water are added. The mixture is then left stirring and evaporating the ethanol formed in the hydrolysis of the TEOS. Finally, 0.667 g of HF (50% aq.) are added. The resulting mixture is heated at 150° C. in autoclaves lined internally with PTFE. After 19 h of heating, the mixture is filtered and 20 g of the ITQ-16 zeolite are obtained for each 100 g of synthesis gel.

Figure 7:
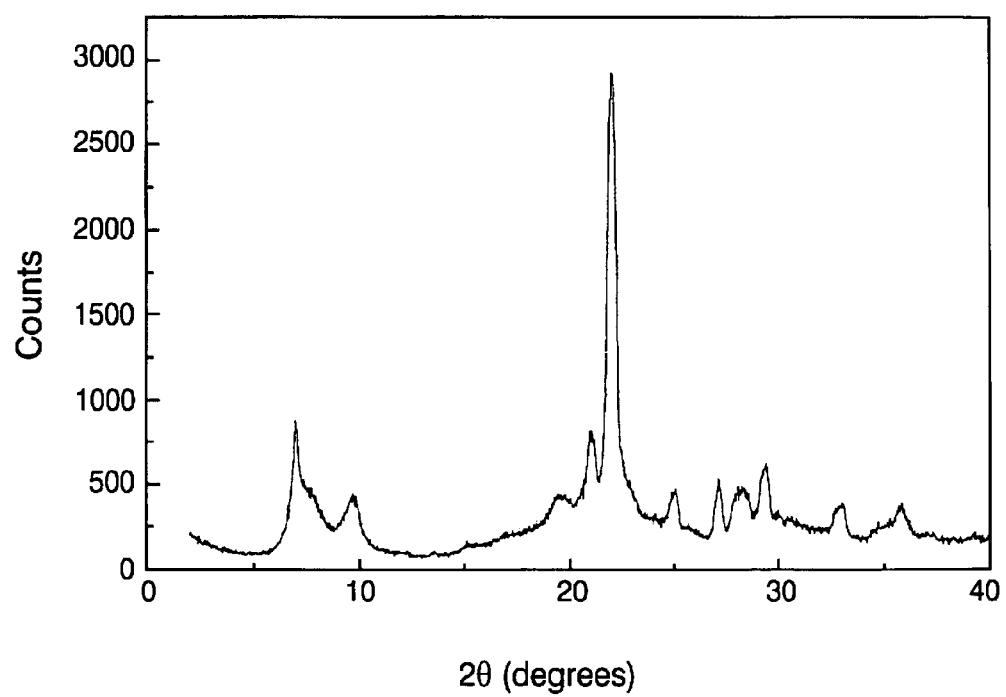
FIG. 7 shows the diffraction pattern of ITQ-16 prepared according to example 3, using the Q-benzyl cation as structure directing agent.

The X-ray diffraction pattern is shown in FIG. 7.

Example 4

This example shows the preparation of ITQ-16 containing Si, Ge and Al, and using the Q-benzyl cation as structure directing agent.

13.67 g of tetraethylorthosilicate (TEOS) are hydrolysed in 26.09 g of an aqueous solution of Q-benzyl ($1.39.10^{-4}$ mols of Q-benzyl(OH)/g). Then 0.457 g of $GeO_2$ and 0.286 g of aluminium isopropoxide are added. The mixture is then left stirring and evaporating the ethanol formed in the hydrolysis of the TEOS, and 7 g of water. Finally, 1.40 g of HF (50% aq.) are added. The resulting mixture is heated in autoclaves lined internally with PTFE at 150° C. After 5 days of heating, the mixture is filtered and 19 g of the ITQ-16 zeolite are obtained for each 100 g of synthesis gel.

Figure 8:
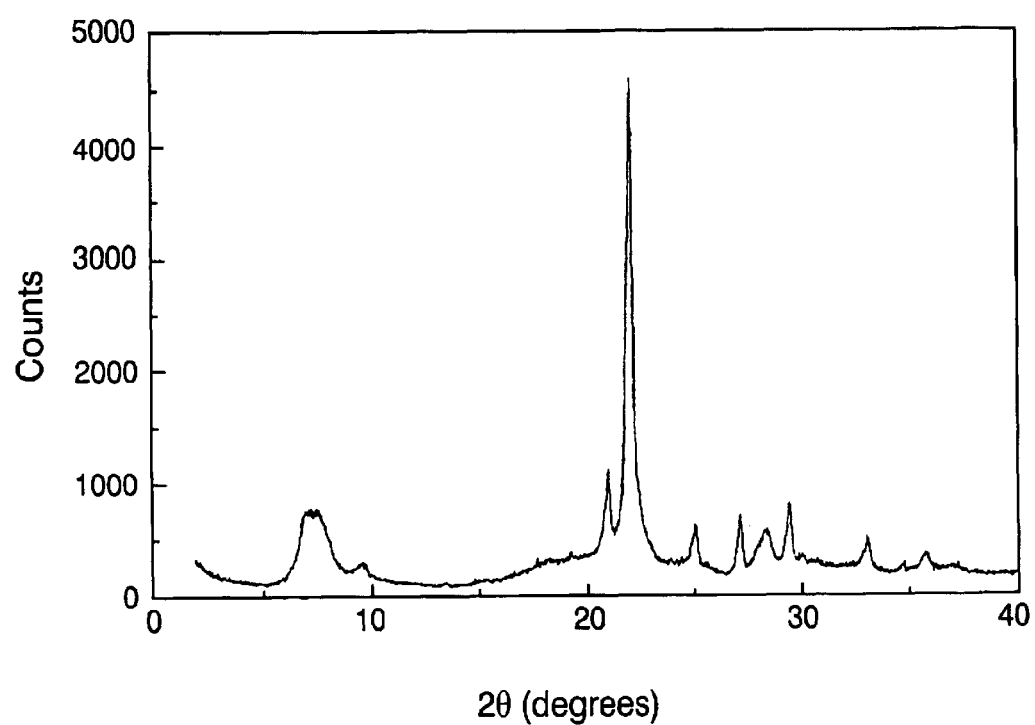
FIG. 8 shows the diffraction pattern of ITQ-16 prepared according to example 4, using the Q-benzyl cation as structure directing agent.

The X-ray diffraction pattern is shown in FIG. 8.

Example 5

This example shows the preparation of ITQ-16 containing Si and Ge, and using the TEA cation as structure directing agent.

30 g of tetraethylorthosilicate (TEOS) are hydrolysed in 39.26 g of an aqueous solution of tetraethylammonium (35%) and 1.5 g of water. Then 3.01 g of $GeO_2$ are added. The mixture is then left stirring and evaporating the ethanol formed in the hydrolysis of the TEOS. Finally, 3.89 g of HF (48% aq.) are added. The resulting mixture is heated at 140° C. in autoclaves lined internally with PTFE in an oven provided with a rotation system (60 rpm). After 48 h of heating, the mixture is filtered and 25 g of the ITQ-16 zeolite are obtained for each 100 g of synthesis gel.

Figure 9:
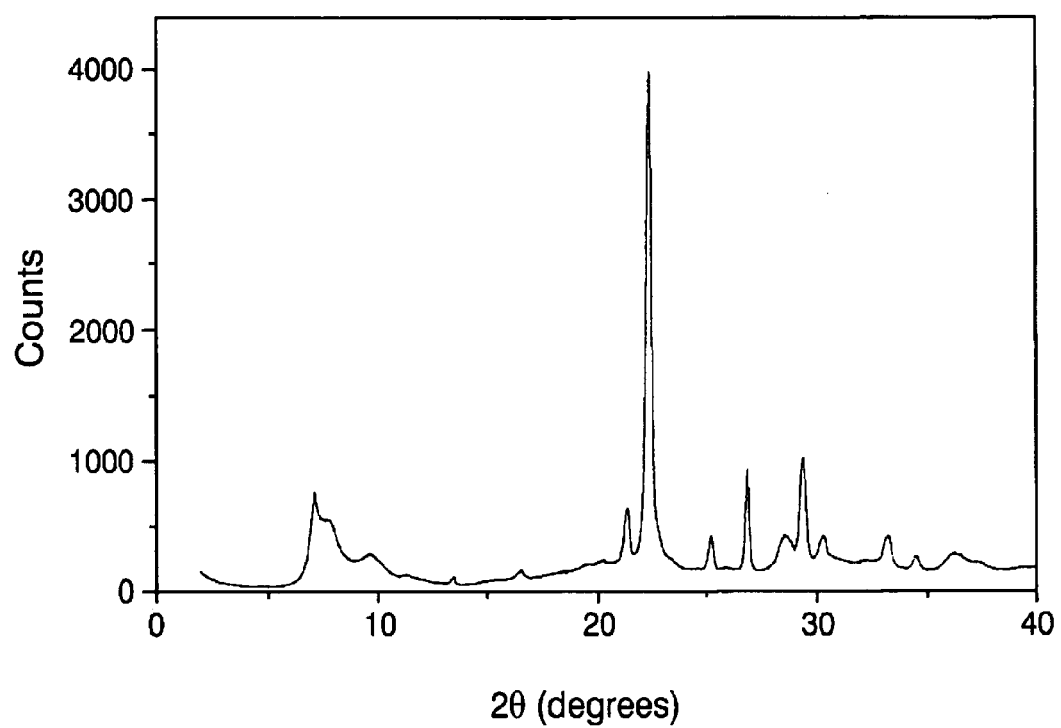
FIG. 9 shows the diffraction pattern of ITQ-16 prepared according to example 5, using the TEA cation as structure directing agent.

The X-ray diffraction pattern is shown in FIG. 9.

Example 6

This example shows the preparation of ITQ-16 containing Si, Ge and Al, and using the TEA cation as structure directing agent.

15 g of tetraethylorthosilicate (TEOS) are hydrolysed in 25.85 g of an aqueous solution of tetraethylammonium (35%). Then 3.77 g of $GeO_2$ and 1.2 g of aluminium isopropoxide are added. The mixture is then left stirring and evaporating the ethanol formed in the hydrolysis of the TEOS. Finally, 2.47 g of HF (50% aq.) are added. The resulting mixture is heated in autoclaves lined internally with PTFE at 140° C. in an oven provided with a rotation system (60 rpm). After 3 days of heating, the mixture is filtered and 23 g of the ITQ-16 zeolite are obtained for each 100 g of synthesis gel.

Figure 10:
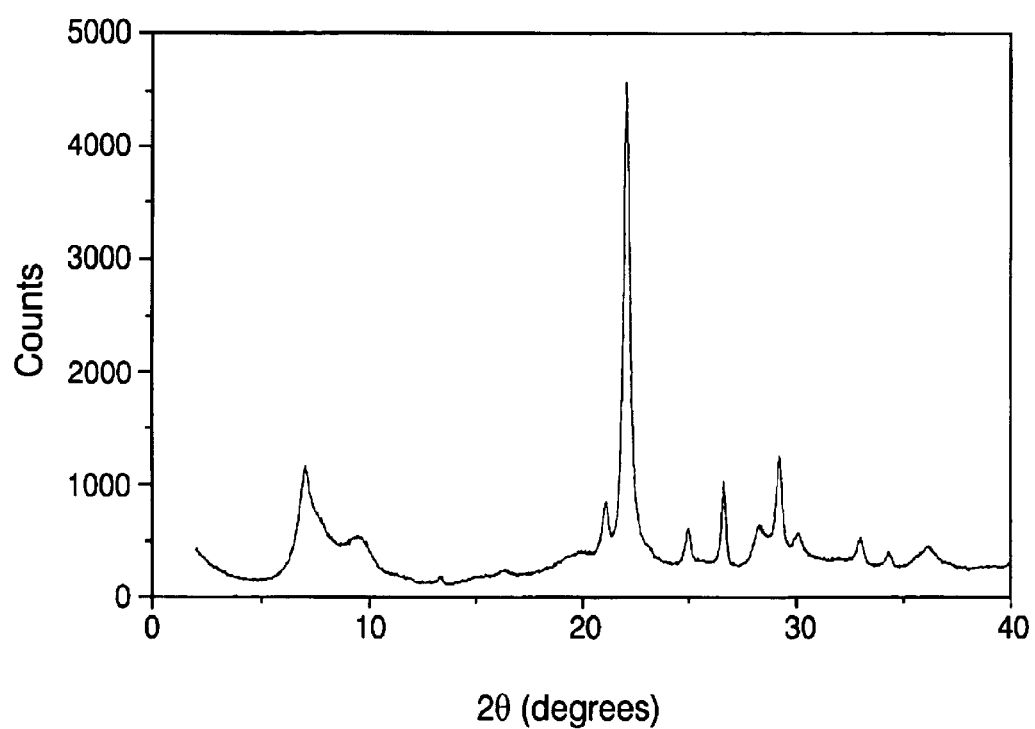
FIG. 10 shows the diffraction pattern of ITQ-16 prepared according to example 6, using the TEA cation as structure directing agent.

The X-ray diffraction pattern is shown in FIG. 10.

Example 7

This example ilustrates the synthesis of ITQ-16 containing Si, B and Ge, and using the DABCO-benzyl cation as structure directing agent.

7.32 g of tetraethylorthosilicate (TEOS) are hydrolysed in 10.1 g of an aqueous solution of DABCO-benzyl ($2.10^{-3}$ mols of DABCO-benzyl(OH)/g) and 0.92 g of water. Then 0.245 g of $GeO_2$, 0.0927 g of boric acid and 1 g of water are added. The mixture is then left stirring and evaporating the ethanol formed in the hydrolysis of the TEOS. Finally, 0.754 g of HF (50% aq.) are added. The resulting mixture is heated at 150° C. in autoclaves lined internally with PTFE. After 7 days of heating, the mixture is filtered and 14 g of the ITQ-5 zeolite are obtained for each 100 g of synthesis gel.

Figure 11:
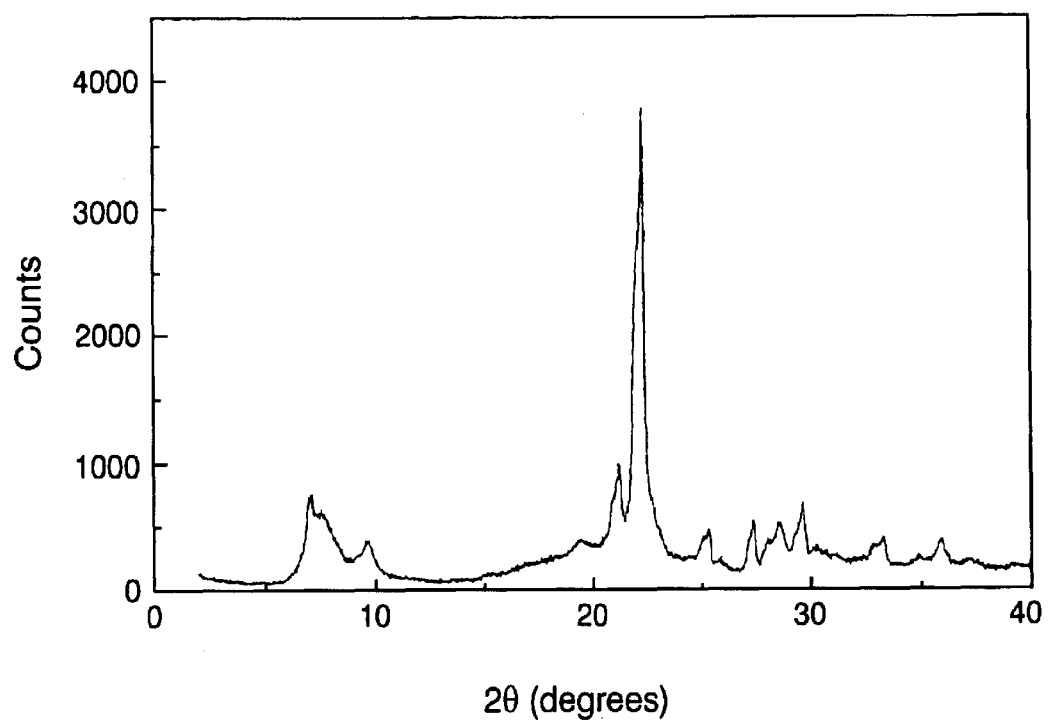
FIG. 11 shows the diffraction pattern of ITQ-16 prepared according to example 7, using the DABCO-benzyl cation as structure directing agent.

The X-ray diffraction pattern is shown in FIG. 11.

What is claimed is:

1. A microporous material, denominated ITQ-16, made up of polymorphs A, B, and C, constitutive of Beta zeolite characterized in that in its calcinated form it has the following empirical formula:

$$x(M_{1/n}XO_2){:}tTO_2{:}gGeO_2{:}(1-g)SiO_2$$

wherein:

T represents one or various elements different of Ge and Si, with +4 oxidation status;

X represents one or various elements with +3 oxidation status and

M represents H⁺ or one or various inorganic cations with charge +n, t is comprised between 0 and 0.1, g is comprised between 0.001 and 0.33, x is comprised between 0 and 0.2, and in that, as synthesised, its X-ray diffraction pattern presents two peaks at angles 2θ of 6.9°, and 9.6°, and a peak around a value of 2θ of 7.4, simultaneously.

2. A microporous material according to claim 1, characterized in that the relative intensity of the peaks at 6.9° and 9.6° with regard to the peak at 7.4° complies with the $I_{9.6°}/I_{7.4°}$ ratio and the $I_{6.9}/I_{7.4}$ ratio being greater than zero and less than ∞.

3. A microporous material according to claim 1, characterized in that it has an X-ray diffraction pattern, as synthesised, with the following values of angle 2θ and relative intensities, I/Io,

| 2θ (degrees) | Intensity |
|---|---|
| 6.93 | w-vs |
| 7.44 | w-vs |
| 9.58 | w-vs |
| 19.32 | w |
| 21.12 | m |
| 21.93 | s |
| 22.19 | vs |
| 25.12 | w |
| 27.15 | w |
| 27.94 | w |
| 28.43 | w |
| 29.46 | w |
| 29.99 | w |
| 32.98 | w |
| 33.11 | w |
| 34.68 | w |
| 35.76 | w |
| 37.12 | w | where w means an intensity of between 0.001 and 20%; m means medium intensity, between 20 and 40%; s means strong intensity, between 40 and 60%, vs means very strong intensity, between 60 and 100%.

4. A microporous material according to claim 1, characterized in that T represents one or various elements in +4 oxidation status selected from the group consisting of Ti, V and Sn.

5. A microporous material according to claim 1, characterized in that X represents one or various elements in +3 oxidation status selected from the group consisting of Al, Ga, B, Cr and Fe.

6. A microporous material according to claim 1, characterized in that M represents a mono or divalent cation in +n oxidation status selected from the group consisting of H⁺, Li⁺, Na⁺, $Ca^{2+}$ and $Mg^2$.

7. A process for the synthesis of a microporous material denominated ITQ-16, made up of polymorphs A, B, and C, constitutive of Beta zeolite which in calcinated form has the following empirical formula:

$$x(M_{1/n}XO_2){:}tTO_2{:}gGeO_2{:}(1-g)SiO_2$$

wherein:

T is one or various elements different of Ge and Si, with +4 oxidation status;

X is one or various elements with +3 oxidation status and

M can be H⁺ or one or various inorganic cations with charge +n, and t is comprised between 0 and 0.1, g is comprised between 0.001 and 0.33 and x is comprised between 0 and 0.2, as defined in claim 1, characterized in that it comprises preparing a reaction mixture comprising at least:

fluoride anions as a mineralising agent, water, a cation selected from the group consisting of TEA, DABCO-benzyl, Q-benzyl and mixtures thereof as structure directing agents, at a pH between 5 and 8.5, and subjecting it to heating at a temperature of between 110° C. and 200° C.

8. A synthesis process according to claim 7, characterized in that the reaction mixture is at a pH between 6 and 8.

9. A synthesis process according to claim 7, characterized in that the reaction mixture is subjected to heating at a temperature of between 130° C. and 175° C.

10. A synthesis process according to claim 7, characterized in that the reaction mixture has a composition in terms of molar ratios within the following ranges:

$H_2O/(SiO_2+GeO_2)$=between 1000 and 0.5,
$HF/(SiO_2+GeO_2)$=between 3 and 0.01,
$(SiO_2+GeO_2)/TO_2$=between 10 and $\infty$,
$(Si+Ge)/X$ is between 5 and $\infty$,
where X represents an element in its trivalent oxidation state, and T represents an element in its tetravalent oxidation state, other than Si and Ge.

11. A synthesis process according to claim 10, characterized in that the ratio $H_2O/(SiO_2+GeO_2)$ is between 100 and 2.

12. A synthesis process according to claim 10, characterized in that the ratio $HF/(SiO_2+GeO_2)$ is between 1 and 0.03.

13. A synthesis process according to claim 10, characterized in that the ratio $(SiO_2+GeO_2)/TO_2$ is between 10 and 10000.

14. A synthesis process according to claim 10, characterized in that the ratio $(Si+Ge)/X$ is greater than 15.

15. A synthesis process according to claim 7, characterized in that the DABCO-benzyl cation is used as a structure directing agent, and in that the reaction mixture has a composition in terms of molar ratios within the following ranges:

DABCO-benzyl/$(SiO_2+GeO_2)$ between 3 and 0.01, $GeO_2/(SiO_2+GeO_2)$, defined as g, between 0.17 and 0.001.

16. A synthesis process according to claim 7, characterized in that the Q-benzyl cation is used as structure directing agent and in that the reaction mixture has a composition in terms of molar ratios within ranges:

Q-benzyl/$(SiO_2+GeO_2)$ between 3 and 0.01, $GeO_2/(SiO_2+GeO_2)$, defined as g; between 0.2 and 0.001.

17. A synthesis process according to claim 7, characterized in that the TEA cation is used as structure directing agent and in that the synthesis mixture has a composition in terms of molar ratios within ranges:

TEA/$(SiO_2+GeO_2)$ between 3 and 0.01, and $GeO_2/(SiO_2+GeO_2)$, defined as g, between 0.33 and 0.001.

18. Synthesis process according to claim 7, characterized in that mixtures of DABCO-benzyl and Q-benzyl cations are used as structure directing agent, and in that the reaction mixture has a composition in terms of molar ratios within ranges:

(DABCO-benzyl+Q-benzyl)/$(SiO_2+GeO_2)$: between 3 and 0.01, $GeO_2/(SiO_2+GeO_2)$, defined as g: between 0.2 and 0.001, and DABCO-benzyl/(DABCO-benzyl+Q-benzyl): between 0 and 1, both excluded.

19. A process selected from the group consisting of a cracking process, hydro-cracking process, hydrocarbon and/or functionalised hydrocarbon soft hydro-cracking process, olefin hydro-isomerization process, a process of alkylation of olefins with isoparaffins and a process of aromatic alkylation with olefins or alcohols, wherein a microporous material defined according to claim 1 is used as a catalyst.

20. The process according to claim 19, characterized in that said aromatic alkylation with olefins is a process of alkylation of benzene with propylene.

21. In processes of selective oxidation of organic compounds using $H_2O$, peroxides or organic hydro-peroxides as oxidants, wherein a microporous material defined according to claim 1 is used as a catalyst.

22. In an oxidation process selected between a Baeyer-Villiger type oxidation process and an Oppenauer oxidation process, wherein a microporous material defined according to claim 1 is used as a catalyst.

23. In a Meerwein-Pondorf-Verley reduction process, wherein a microporous material defined according to claim 1 is used as a catalyst.

24. In a process for the elimination of organic vapours (VOC), wherein a microporous material defined according to claim 1 is used as a component of the catalysts for such process.

25. In a process for the epoxidation of olefins, using organic or inorganic hydroperoxide, such as for example $H_2O_2$, tertbutylhydroperoxide, cumene hydroperoxide, as oxidating agents in an oxidation process selected from the group consisting of an alkane oxidation process, a process of alcohol oxidation and a process of oxidation of thioethers to sulphoxides and sulphones, wherein a microporous material defined according to claim 1 that includes Ti, is used as a catalyst for such process.

26. In a process selected between a Bayer-Villiger oxidation process using $H_2O_2$ as an oxidating agent and a process of ammoximation from cyclohexanone to cyclohexanone oxime with $NH_3$ and $H_2O_2$, wherein a microporous material defined according to claim 1 containing Sn, is used as a catalyst.

* * * * *